US00PP09490P

United States Patent [19]

Endisch et al.

[11] Patent Number: Plant 9,490

[45] Date of Patent: Mar. 26, 1996

[54] GERANIUM PLANT NAMED 'ARENO'

[75] Inventors: Gerd Endisch, Geranienweg, D-76767 Hagenbach; Ursula Endisch-Burmeister, Bad Kreuznach, both of Germany; Wolf Endisch, Valle Guerra/Teneriffa, Spain

[73] Assignee: Gerd Endisch, Hagenbach, Germany

[21] Appl. No.: 384,160

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,717 4/1989 Duemmen ..... Plt./87.12

P.P. 8,304 7/1993 Schumann ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Areno' is characterized by a pink flower color, a dark red eye on all pedals, dark foliage without zonation, a compact habit, early flower response and heat tolerance.

1 Drawing Sheet

BACKGROUND OF THE NEW PLANT

The present invention comprises a new and distinct cultivar of geranium botanically known as *Pelargonium zonale*, and hereinafter referred to by the cultivar name 'Areno'.

'Areno' is a product of planned breeding program which had the objective of creating new geranium cultivars with pink flower color with dark foliage, heat resistance, semi-double flower form.

'Areno' was originated from a hybridization made in a controlled breeding program in Hagenbach, Germany, in 1990. The female parent was 'Epos', characterized by its light pink flower color with red markings, medium green foliage without zonation and semi-double flower form. 'Epos' was patented in Germany, but is no longer commerically available. As compared with 'Epos', 'Areno' has a darker pink flower color, the red markings on the petals are larger, the leaves are darker and show more zonation. The male parent of 'Areno' was 'Rio', characterized by its pink flower color with an eye, single flower form, dark foliage and weak habit. 'Rio' is not patented in the United States and is not commercially available.

'Areno' was discovered and selected as one flowering plant within the progeny of the stated cross by the inventors in August 1991 in a controlled Environment in Hagenbach, Germany.

DESCRIPTION OF THE NEW PLANT

The first act of asexual reproduction of 'Areno' was accomplished when vegetative cuttings were taken from the initial selection in January 1992 in a controlled environment in Hagenbach, Germany, by a technician working under formulations established and supervised by Gerd Endisch.

Horticultural examination of selected units initated in May 1992 has demonstrated that the combination of characteristics as herein disclosed for 'Areno' are firmly fixed and are retained through successive generations of asexual reproduction.

'Areno' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. measurements and dimensions given below are approximate.

The following traits have been repeatedly observed and are determined to be basic characteristics of 'Areno' to distinguish this geranium as a new and distinct cultivar:

1. pink flower color
2. dark red eye in all petals
3. dark foliage without zonation
4. compact habit
5. early flower response
6. heat tolerance Of the many commercial cultivars known to the present inventor, the most similar in comparison to 'Areno' is 'Bravo'. Reference is made to Chart A below which compares certain characteristics of 'Areno' to those same characteristics of 'Bravo'. In comparison to 'Bravo', 'Areno' has a smaller umbel, shorter peduncle and peduncle length, lighter pink and darker eye in the petal, shorter internodes.

BRIEF DESCRIPTION OF THE DRAWING

The accompanying photographic drawing shows typical flower and foliage characteristics of 'Areno', with colors being as true as possible with illustrations of this type.

DETAILED BOTANICAL DESCRIPTION

In the following description color references are made to The Royal Horticultural Society Color Chart (R.H.S.). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zonal geranium, cv. 'Aveno'.

Inflorescence:

*Umbel.*—Comprises approx. 40 flowers.

*Average diameter.*—Approx. 80–85 mm.

*Average depth.*—Approx. 44–46 mm.

*Spring flowering response period.*—In Hannover (Bundessortenamt), in 1994, first flower observed April 18.

*Outdoor flower production.*—The flower count in 1993 indicated between 65–70 flowers per plant for May 15 through August 15 observation period.

*Durability.*—Good rain resistance.

*Peduncle length.*—Approx. 115 mm.

Corolla:

*Blooming habit.*—Continuous, until frost destroys plant.

*Average diameter.*—Approx. 44–46 mm.

*Form.*—Semi-double; cup shaped when bloom first opens, flattening to shallow cup with maturity.

*Petals.*—Normally 6–7.

*Color: (General tonality from a distance of three meters).*—Pink with dark eye.

*Petal color (upper surface).*—R.H.S. 73 C, dark eye R.H.S. 66 A, white base with stripes; the eye of the lower petals in smaller.

*Petal color (lower surface).*—R.H.S. 69 B.

Width.—Approx. 21 cm across.

*Pedicel length.*—Approx. 24–26 mm.

*Pedicel color.*—Light red (anthocyanin colored).

Bud:

*Size.*—Approx. 1.2–1.5 cm across.

*Shape.*—Initially ovate.

*Color.*—Green with anthocyanin at the base.

*Sepals.*—Give; pointed linear lanceolate; at time of petal appearance, approx. 9 mm in length.

Reproductive organs:

Stamens.— Anthers: 7–9 in number. Filaments: Approx. 5–7 mm in length. Pollen: Orange.

*Pistil.*— No.: One. Length: Approx. 9 mm in length. Stigma: 5–6 lobes; red. Style: Approx. 3 mm in length; red.

*Ovaries.*—Green.

*Fruit.*—Partially fertile.

Plant:

*Foliage.*—Abundant quantity. Size: Approx. 7–8 cm across. Margin: Bicrenate. Texture: Leathery; pubescence on bottom side along veins about 2 mm in length. Ribs and veins: Distinct venation on bottom side, not prominently different on top surface. Color (upper surface): R.H.S. 137 A/B, dark foliage. Color (zonation): None. Color (bottom surface): R.H.S. 137C. Petioles: Approx. 6–7cm in lenght; green.

*General appearance and form.*—Bushy, compact habit. Internode length: Approx. 14–16 mm. Branching pattern: Self branching from base, very good branching characteristic; in 1994, 14 branches observed Aug. 15. Height: Approx. 18–20 cm from media surface. Strength: Good shipping ability as rooted or unrooted cuttings; good heat tolerance.

CHART A

| | New Cultivar Name: 'Areno' | Comparison Cultivar Name: 'Bravo' |
|---|---|---|
| Umbel diameter | 80–85 mm | 90–95 mm |
| Depth | 44–46 mm | 56–58 mm |
| Penduncle length | 115 mm | 175 mm |
| Pedicel length | 24–26 mm | 34–36 mm |
| Internode length | 14–16 mm | 26–28 mm |

What is claimed is:

1. A new and distinct cultivar of geranium plant known as 'Areno', as described and illustrated and particularly characterized by a pink flower color, a dark red eye on all pedals, dark foliage without zonation, a compact habit, early flower response and heat tolerance.

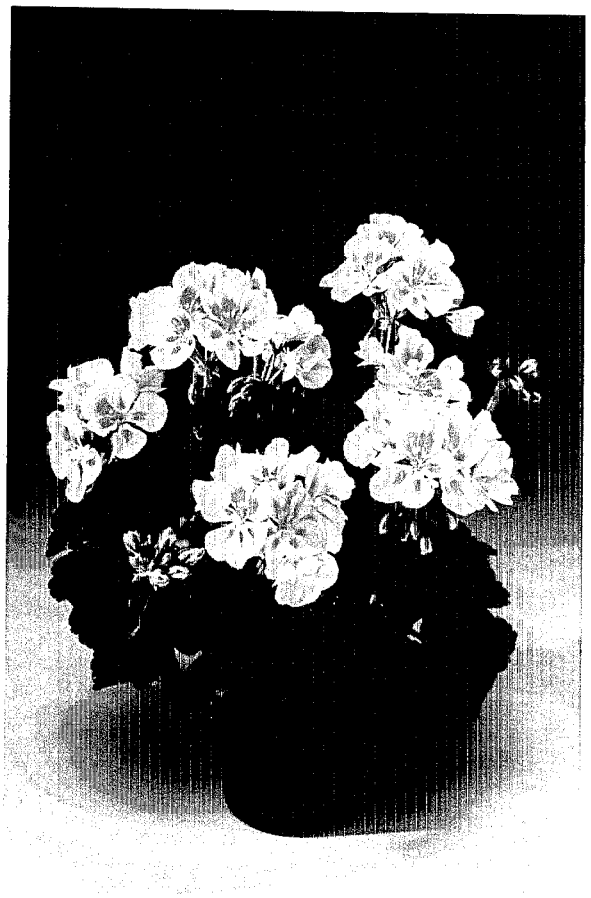

* * * * *